United States Patent [19]

Klainer

[11] Patent Number: 5,107,133
[45] Date of Patent: Apr. 21, 1992

[54] RESERVOIR CHEMICAL SENSORS WITH REMOVABLE RESERVOIR CELLS

[75] Inventor: Stanley M. Klainer, Henderson, Nev.

[73] Assignee: FiberChem Inc., Las Vegas, Nev.

[21] Appl. No.: 576,604

[22] Filed: Aug. 31, 1990

Related U.S. Application Data

[63] Continuation-in-part of Ser. No. 544,681, Jun. 27, 1990.

[51] Int. Cl.⁵ ............................................. G01N 15/06
[52] U.S. Cl. ................................. 250/573; 356/246
[58] Field of Search .............. 250/573, 574, 575, 576; 356/244, 246

[56] References Cited

U.S. PATENT DOCUMENTS 2,483,876 10/1949 Boyer .................................. 250/573
2,898,802 8/1959 Ljungberg et al. ................. 250/573
3,764,214 10/1973 Heiss .................................. 356/246

Primary Examiner—David C. Nelms
Attorney, Agent, or Firm—Henry P. Sartorio

[57] ABSTRACT

A reservoir chemical sensor has a sensor body containing a reservoir cell channel around which source and detector are positioned within the cell body. A replaceable modular reservoir cell which contains sensing solution fits snugly and removably in the channel in the sensor body. Different reservoir cells can be easily inserted and removed from the sensor body.

20 Claims, 8 Drawing Sheets

RESERVOIR CHEMICAL SENSORS WITH REMOVABLE RESERVOIR CELLS

RELATED APPLICATIONS

This application is a continuation in part of U.S. patent application Ser No 544,681 filed June 27, 1990.

BACKGROUND OF THE INVENTION

The invention relates generally to chemical sensors and more particularly to reservoir chemical sensors.

The need for a universal in-situ sensor capable of working with a variety of light interaction techniques (luminescence, absorption, reflection, refraction, Raman and scattering) and using any available sensing chemistry (organic, inorganic, bio-organic, bio-inorganic and genetic) indicates the desirability of an improved reservoir chemical sensor. The sensor should have the capacity to perform qualitative and quantitative analysis, high resolution, long active lifetimes (with both reversible and irreversible chemical interactions) and good reproducibility between sensors for a particular species. The sensing reagents are in liquid form, either liquid themselves, or solids, liquids or gases dissolved in a solvent. The key elements of the sensor can and should be very accurately controlled. The reagent solution can be made with a very high degree of repeatability; the active volume of the reservoir can be precisely controlled and the intensity of the illuminating source and the sensitivity of the detector are accurately known. Reservoir sensors are needed which can incorporate all these features and advantages into a flexible, practical design.

Initial reservoir chemical sensors using fiber optics (reservoir FOCS) are illustrated by U.S. Pat. No. 4,757,343 to Hirshfeld and U.S. Pat. No. 4,666,674 to Miller, et al. which show typical reservoir FOCS formed by attaching a capillary tube coaxially to the end of an optical fiber using a gas bubble or membrane to close the tube. This structure is laborious to assemble accurately, difficult to control and use, and impossible to reproduce uniformly. U.S. Pat. No. 4,892,383 to Klainer, et al and U.S. patent application Ser. No. 503,463 by Klainer, et al. provide an improved reservoir FOCS having a modular design. Although very practical to construct and uncomplicated to use, its applications are restricted by the use of fiber optics to transmit light signals into and out from the sensor to remote sources and detectors.

U.S. patent application Ser. No. 544,681 by Klainer, et al. describes a class of reservoir chemical sensors in which the source and detector are mounted within the cell body, thereby eliminating the need for fiber optics. The reservoir chemical sensor is formed with a modular sensor body which contains a sensing reagent therein in a channel or chamber formed within the sensor body. The species of interest enters into the sensor body through a semi-permeable membrane; alternatively the species may enter through an inlet port. The source and detector are mounted within the cell body itself; protective windows may be used to separate the source and detector from the sensing reagent. This design offers many advantages; however, the reservoir is integral to the sensor body. The sensor can be used for another chemistry, but this requires flushing out the sensing solution, cleaning the cell and replacing with a new sensing solution. If a membrane of different selectivity is required, the membrane must also be replaced. Unless the steps of converting the sensor from one chemistry to another are taken, a plurality of complete sensors, each for a specific chemistry, are required. It would, therefore, be highly desirable to have a reservoir sensor design in which a variety of chemistries can be readily interchanged.

SUMMARY OF THE INVENTION

Accordingly, it is an object of the invention to provide an improved reservoir chemical sensor.

It is also an object of the invention to provide a reservoir chemical sensor design which permits easy exchange of sensing reagent.

The invention is an improved reservoir chemical sensor having a removable modular reservoir cell which may be readily inserted into or removed from the sensor body. The reservoir chemical sensor is formed of a sensor housing or body which contains a reservoir cell channel formed therein; a replaceable modular cell which contains the sensing reagent fits snugly within the channel and is easily removed or inserted. One or more sources and one or more detectors are mounted within the cell body around the channel in a variety of orientations (e.g. linear or at right angles) so that when the reservoir cell is placed within the channel, an optical signal is input into the reservoir cell and a detector signal is obtained. The sample enters the reservoir cell through a membrane formed in the cell which communicates with a sample flow channel in the sensor body or through other inlet means formed in the cell.

DETAILED DESCRIPTION OF THE PREFERRED EMBODIMENTS

Figure 1A:
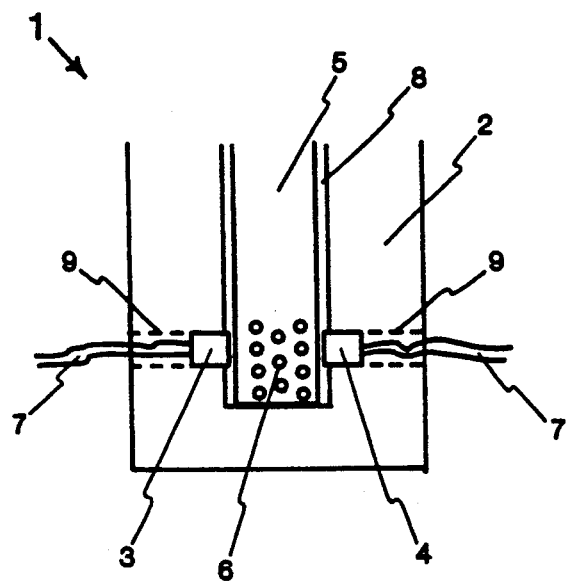
FIGS. 1A and 1B are side and top cross-sectional views of a reservoir chemical sensor with removable reservoir cell, according to the invention.
Figure 1B:
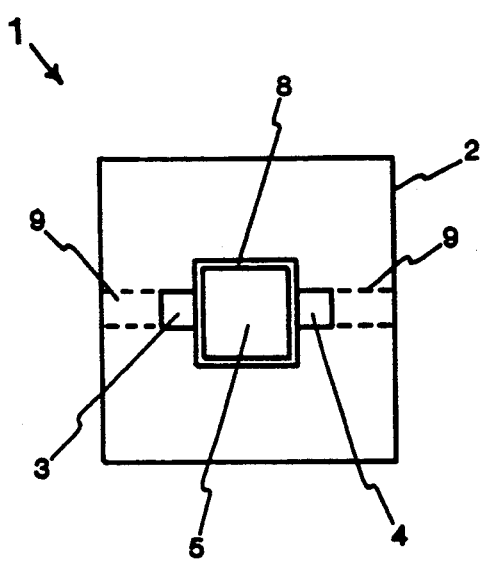

As show in FIGS. 1 A,B reservoir chemical sensor 1 is formed of a sensor housing or body 2 which has formed therein a channel 8 in which a removable cell 5 snugly fits. A source 3 and detector 4 are mounted in sensor body 2, e.g., in channels 9, with electrical connections 7 passing therethrough which connect the source and detector to a suitable power supply, control means and processing means. The light source 3 and detector 4 are mounted in a fixed orientation around the channel 8 so that when reservoir cell 5 containing a sensing solution with analyte 6 is positioned in channel 8, the light source 3 directs a light signal into the solution 6 and detector 4 receives a light signal from solution 6. As shown, source 3 and detector 4 are in a linear arrangement on opposite sides of reservoir cell 5; however other source/detector arrangements can be used. As shown in FIG. 1B, housing 2 and cell 5 have a square cross-section; however, other shapes can be used.

Chemical sensor 1 thus provides for easy interchange of reservoir cell 5. The sensing chemistry is all contained within the reservoir cell 5. All reservoir cells of the same size and shape can be utilized with sensor 1 which contains source 3 and detector 4 in proper alignment for the measurements. Thus, many different chemistries can be measured using only one sensor, by using a plurality of interchangeable reservoir cells, each containing a different chemistry, within the sensor.

Figure 2A:
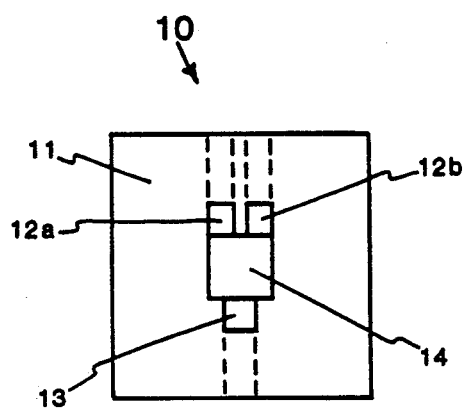
FIGS. 2A, 2B and 2C are top cross-sectional views of the reservoir chemical sensor with removable cell showing various combinations of one and/or two sources and/or detectors in a linear arrangement.
Figure 2B:
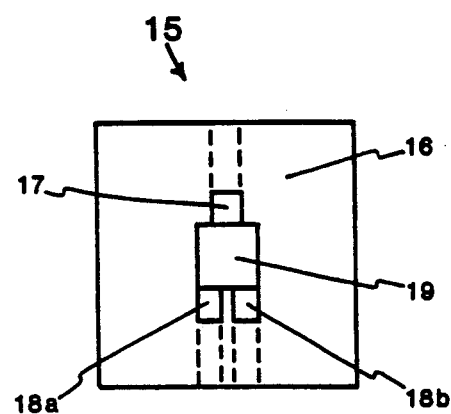
Figure 2C:
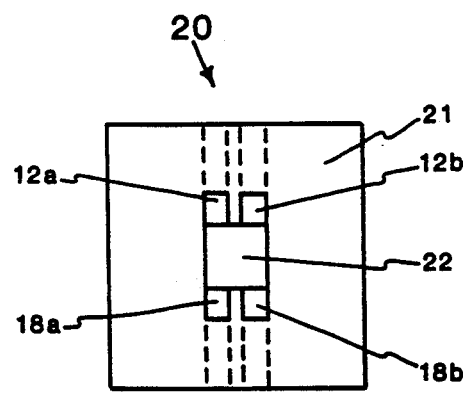

FIGS. 2A-C show other linear source/detector combinations than the single source/single detector of FIGS. 1A,B. As shown in FIG. 2A, sensor 10 is made of cell body 11 with reservoir cell 14 positioned therein. A pair of sources 12a,b are positioned on one side of cell 14 and a single detector 13 is positioned on the other side. As shown in FIG. 2B, sensor 15 is made of cell body 16 with reservoir cell 19 positioned therein. A single source 17 is positioned on one side of cell 19 and a pair of detectors 18a,b are positioned on the other side. As shown in FIG. 2C, sensor 20 is made of sensor body 21 with reservoir cell 22 and has a pair of sources 12a,b on one side of cell 22 and a pair of detectors 18a,b on the other side. Multiple sources and detectors are used for multiple input signals (e.g., two wavelength excitation) or multi-output measurements (e.g., two different responses).

Figure 3A:
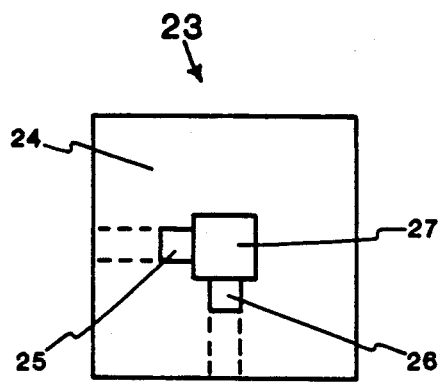
FIGS. 3A, 3B, 3C and 3D are top cross-sectional views of the reservoir chemical sensor with removable reservoir cell showing various combinations of one and/or two sources and/or detectors in a right angle configuration.
Figure 3B:
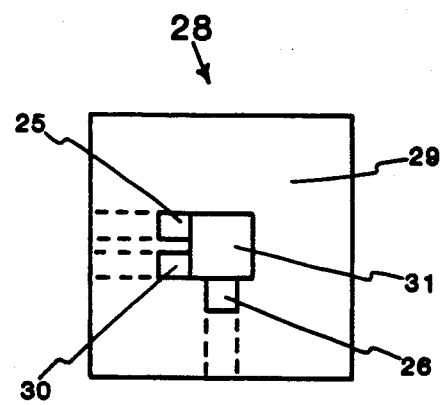
Figure 3C:
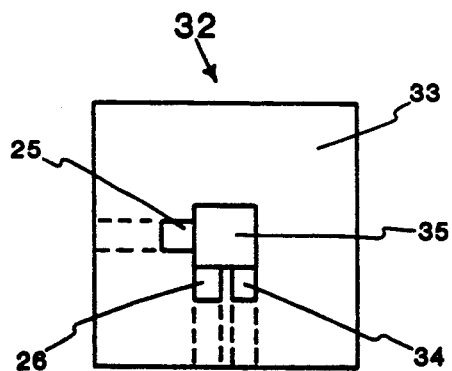
Figure 3D:
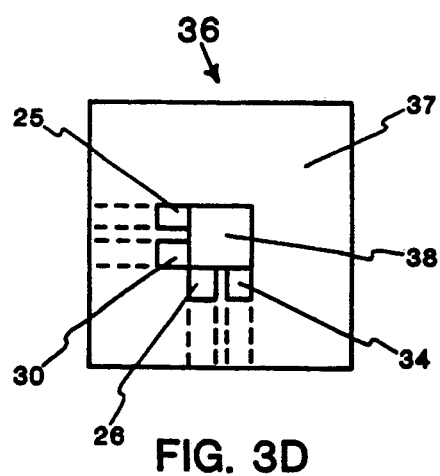

In addition to the linear arrangements of source and detector as previously described, the source and detector may be positioned at right angles as shown in FIGS. 3A-D. Some applications, such as Raman or fluorescence are best performed with the orthogonal arrangement. In FIG. 3A, sensor 23 has a single source 25 and single detector 26 positioned at right angles around cell 27 in sensor body 24. In FIG. 3B, sensor 28 has a pair of sources 25, 30 and a single detector 26 positioned at right angles to the sources 25, 30 around cell 31 in sensor body 29. In FIG. 3C, sensor 32 has a single source 25 and a pair of orthogonal detectors 26, 34 around cell 35 in sensor body 33. In FIG. 3D, sensor 36 has a pair of sources 25, 30 and a pair of detectors 26, 34 orthogonally oriented to the sources 25, 30 around cell 38 in sensor body 37.

Figure 4A:
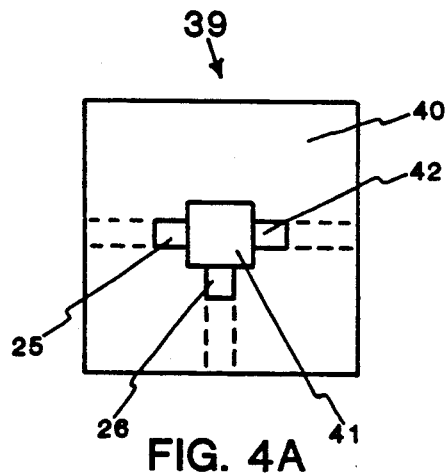
FIGS. 4A and 4B show top cross-sectional views of the reservoir chemical sensor with removable reservoir cell with both a linear and right angle detector.
Figure 4B:
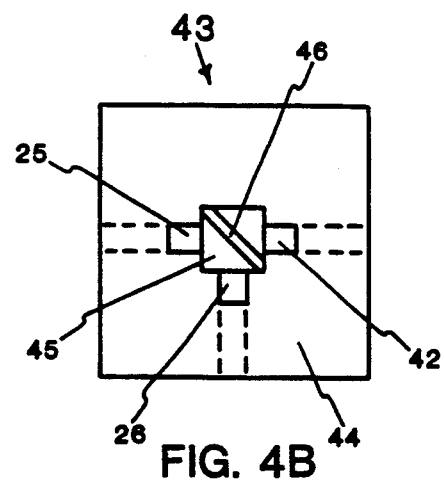

The linear and orthogonal source/detector arrangements previously described can be combined as shown in FIG. 4A. For example, an absorption measurement could be made with the linear configuration while a fluorescence measurement is performed with the orthogonal configuration. Reservoir chemical sensor 39 has a source 25 and a detector 26 aligned at right angles to source 25 and a detector 42 aligned linearly with source 25 around cell 41 in sensor body 40. Sensor 43, shown in FIG. 4B, is similar to sensor 39 and has the same arrangement of source 25 and detectors 26 and 42; however, reservoir cell 45 is divided by a dichroic mirror or beam splitter 46 in order to provide the appropriate beams to the detectors 26 and 42. Dichroic mirror or beam splitter 46 is placed within cell 45 and thus must be chemically compatible with the sensing reagent. Alternatively, reservoir cell 45 could be replaced by a pair of triangular cross-section reservoir cells with the dichroic mirror or beam splitter 26 placed therebetween so that contact with the sensing solution is eliminated.

Figure 5A:
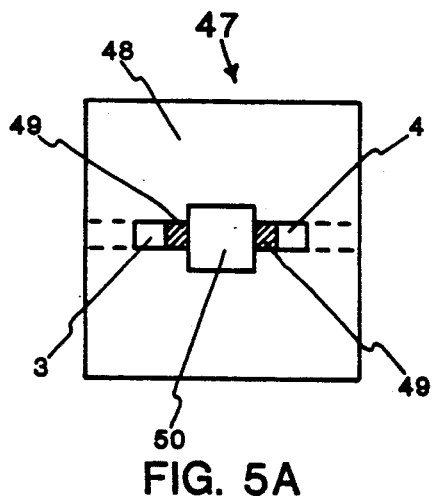
FIGS. 5A, 5B, 5C and 5D show top cross-sectional views of the reservoir chemical sensor with removable cell having various optical components between the source and detector and the reservoir cell.
Figure 5B:
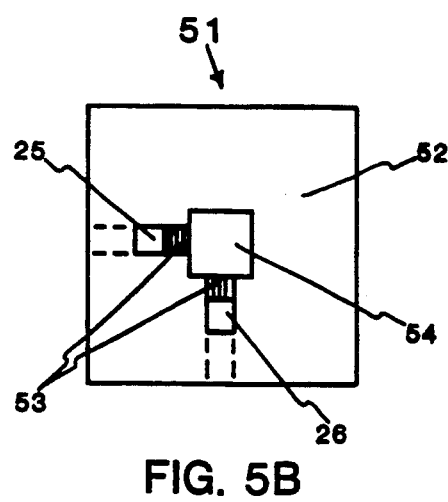
Figure 5C:
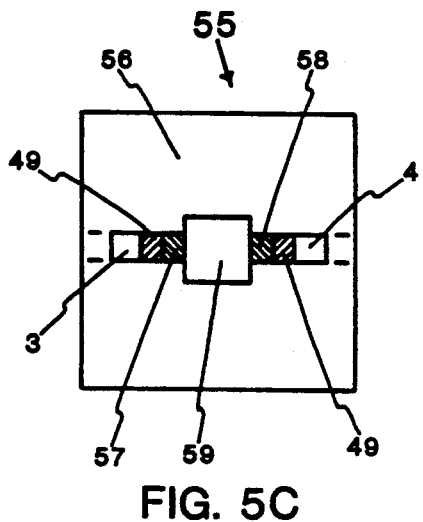
Figure 5D:
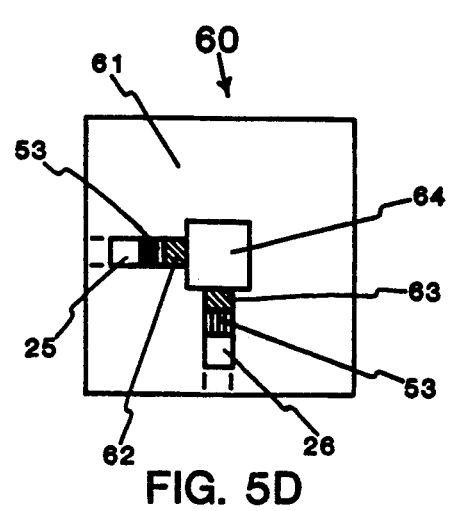

Other optical components may be used in combination with the source and/or detector to facilitate and enhance measurement capability as shown in FIGS. 5A-D. In FIG. 5A, sensor 47 with sensor body 48 and reservoir cell 50 has a simple linear arrangement of source 3 and detector 4 with the addition of collimating lenses 49 between the source 3 and detector 4 and the reservoir cell 50. In FIG. 5B, sensor 51 with sensor body 52 and reservoir cell 54 has a simple orthogonal arrangement of a single source 25 and detector 26, and further include a diverging lens 53 between the source 25 and detector 26 and the reservoir cell 54. As shown in FIG. 5C, sensor 55 has the previously described combination of source 3 with collimating lens 49 and detector 4 with collimating lens 49 in a linear arrangement (as shown in FIG. 5A) around cell 59 in sensor body 56 with the addition of a source color filter 57 and a detector color filter 58 between the source and detector and the cell 59. In FIG. 5D, sensor 60 with sensor body 61 and reservoir cell 64 has a source 25 with diverging lens 53 and orthogonal detector 26 with diverging lens 53 similar to FIG. 5B with the addition of a source color filter 62 and a detector color filter 63 between the source and detector and the cell 64. While various combinations of source, detector and additional optical components have been shown in FIGS. 5A-D, these embodiments are illustrative and not exhaustive of all possible combinations. The elements may not be used with both source and detector in every case and different combinations of optical elements with different source/detector arrangements may be used. The collimating optics are generally used with the linear source/detector arrangement while the diverging optics are generally used with the orthogonal source/detector arrangement.

Figure 6D:
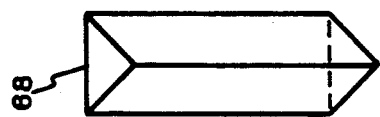
FIGS. 6A, 6B, 6C and 6D show various reservoir cell designs of rectangular, circular and triangular cross-section.
Figure 6C:
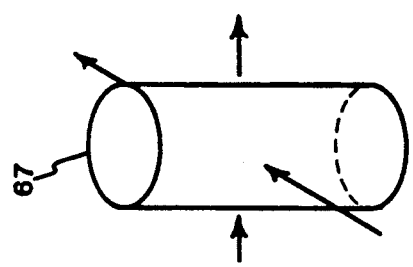
Figure 6B:
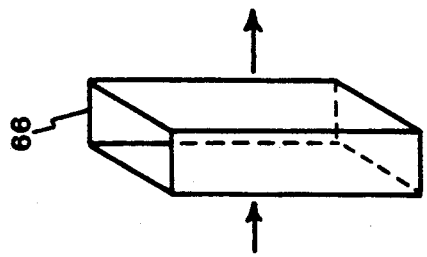
Figure 6A:
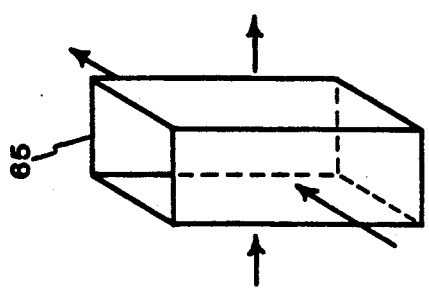

The reservoir cells according to the invention, may be of a variety of geometries and sizes. All cells of a particular size and shape will fit into the sensor housing designed for that size and shape cell and can be readily interchanged therein. The illustrative embodiments previously described showed a reservoir cell having a square horizontal cross-section FIGS. 6A,B show reservoir cells 65 and 66 having a rectangular cross-section of different widths. Cell 65 has relatively long length and width and typically light could pass through the cell in either horizontal direction. Cell 66 has a much narrower width and would typically be used when the penetration depth of the light into the sensing solution is very small so that measurements would generally be performed along the short direction of the cell. Several thin rectangular cells 66 could be stacked together to form a thicker cell having a plurality of separate chemistries therein. FIG. 6C shows a cell 67 having a circular cross section and FIG. 6D shows a cell 68 having a triangular cross section. As previously described with reference to FIG. 4B, a pair of triangular cells 68 could be used to form the reservoir cell 45 with a dichroic mirror or beam splitter 46 between the two triangular cells.

Figure 7D:
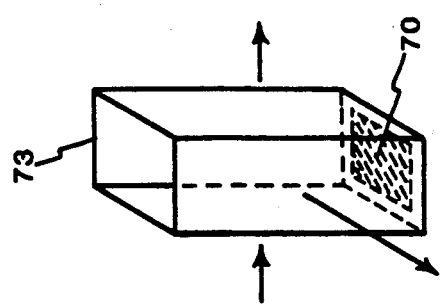
FIGS. 7A, 7B, 7C and 7D show reservoir cells with semi-permeable membranes.
Figure 7C:
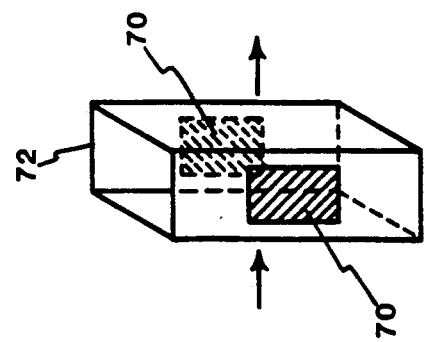
Figure 7B:
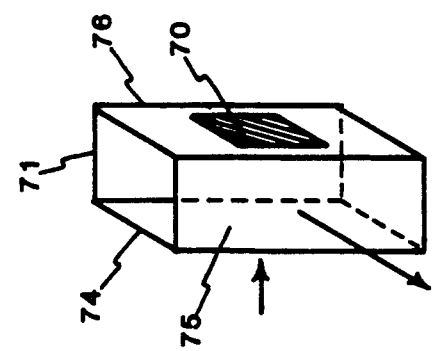
Figure 7A:
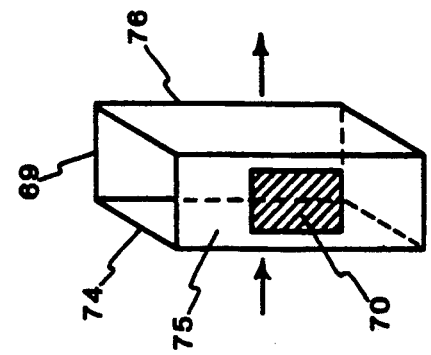

The species of interest may enter the reservoir cells through a semi-permeable membrane which passes the species of interest but contains the sensing solution within the cell. The cell designs containing membranes are shown in FIGS. 7A-D. In FIG. 7A, cell 69 has a membrane 70 on one side wall 75 thereof. Since light will not pass through the membrane, typically, the membrane must be positioned on a lateral wall which does not interfere with the optical measurement. In cell 69, light enters through face 74 and exits through opposed face 76 in a linear arrangement so membrane 70 is placed on surface 75 between opposed faces 74, 76. In FIG. 7B, cell 71 is configured so that light is input from lateral face 74 and light is detected through orthogonally adjacent face 75 so the membrane 70 is placed on opposed face 76. Cell 72 of FIG. 7C is a pass-through cell having a pair of membranes 70 on opposed faces of cell 72 so that the species of interest may pass into the cell through one membrane and pass out through the other membrane. Light transmission will be through the pair of opposed faces between the faces having the membranes therein. In FIG. 7D, cell 73 has the membrane placed in the bottom surface so that optical measurements can be made from any of the four lateral surfaces. The membrane could similarly be placed on the top, or on both top and bottom.

Figure 8:
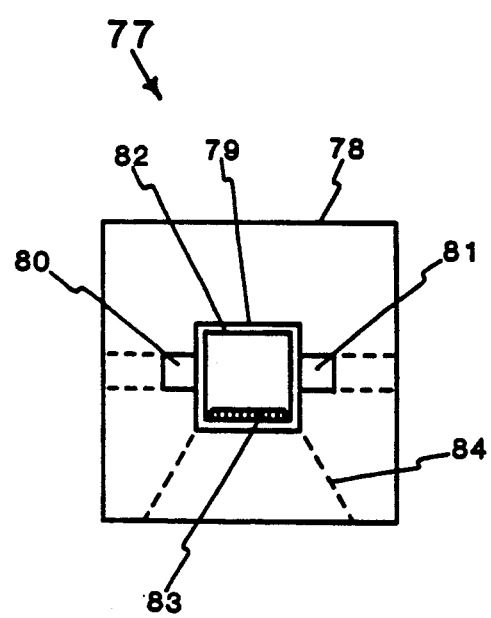
FIG. 8 shows a top cross sectional view of a reservoir chemical sensor with removable reservoir cell having a semi-permeable membrane in the cell.

A reservoir chemical sensor 77 for use with a removable modular reservoir cell 82 having a semi-permeable membrane 83 on a face thereof is shown in FIG. 8. Reservoir cell 82 fits into reservoir cell channel 79 of sensor body 78; source 80 and detector 81 are positioned within cell sensor body 78. The sensor body 78 further includes a sample flow channel 84 formed therein which allows sample to pass through the cell body 78 and contact the semi-permeable membrane 83 of reservoir cell 82. Although only a single membrane cell has been illustrated, cells with additional membranes would require a sensor body with a plurality of sample flow channels to allow the sample to contact the membranes. (FIGS. 1A,B and 8 show a gap between the cell and channel for ease of illustration, but typically, the cell will fit snugly into the channel for proper alignment and to prevent leakage of sample at the sample channel/membrane interface.)

Figure 9A:
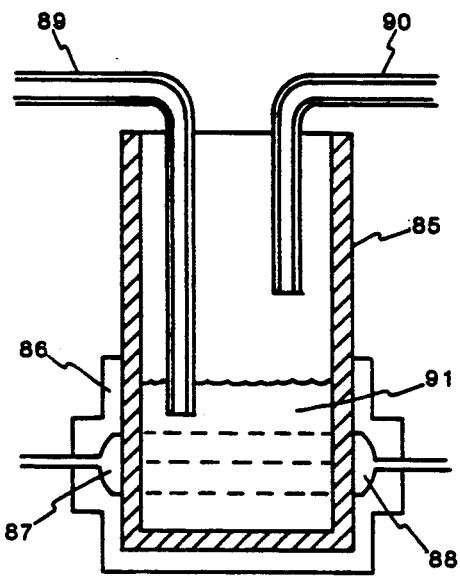
FIGS. 9A, 9B, 9C and 9D are side cross-sectional views of a reservoir chemical sensor with removable reservoir cell showing various sample inlet and sample pretreatment means.
Figure 9B:
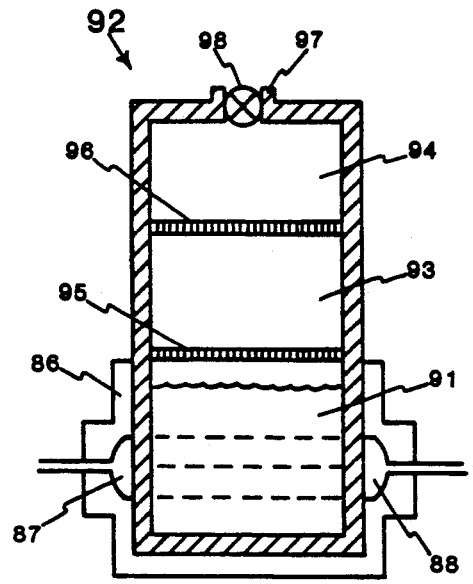
Figure 9C:
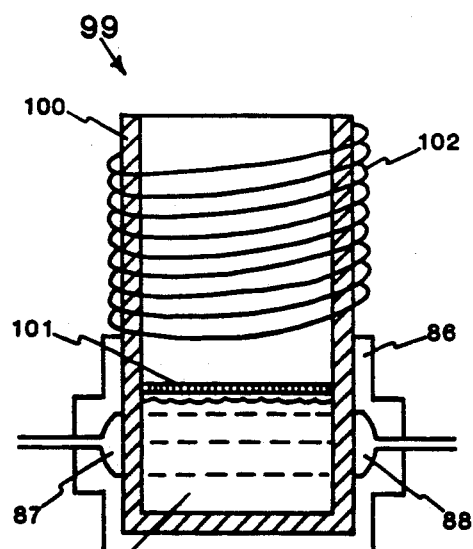
Figure 9D:
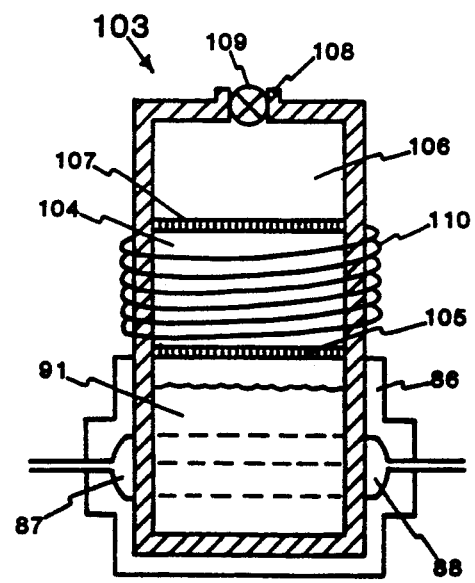

The reservoir cell can utilize other means for introducing the sample into the cell, including a variety of sample preparation means, as illustrated in FIGS. 9A-D As shown in FIG. 9A, reservoir cell 85 is placed within sensor body 86 which contains a source 87 and detector 88. A sample inlet pipe 89 extends into reservoir cell 85 and a sample removal pipe 90 extends out of cell 85. For a gaseous sample, the sample inlet pipe 89 extends into the cell below the level of the sensing solution 91 so that the input sample can be bubbled through the sensing solution 91; removal pipe 90 does not extend into solution 91 to remove the sample. In a continuous replenishment system where sample and sensing solution are continuously flowed through the cell, the removal pipe 90 would extend into the solution. In FIG. 9B, a reservoir cell 92 containing a sensing reagent 91 is mounted in a sensor body 86 with source 87 and detector 88 mounted therein. Reservoir cell 92 has sample preparation chambers 93, 94 above the sensing solution 91 at the lower end of the cell 92. A sample chamber 93 is formed in (or attached to) the cell 92 above the sensing solution 91 and a solvent chamber 94 is formed in (or attached to) cell 92 above sample chamber 93. The sample chamber 93 is separated from the sensing solution 91 by a porous plate or membrane 95 and the solvent chamber 94 is separated from sample chamber 93 by a porous plate or membrane 96. In operation, a solid sample is placed in sample chamber 93 and a leaching solution is introduced into solvent chamber 94 through inlet port 97 which is controlled by valve 98. The leaching solvent passes through porous plate or membrane 96 and interacts with the solid sample in chamber 93. The solvent dissolves or reacts with the solid sample. The dissolved sample or reaction product passes through porous plate or membrane 95 into the sensing solution 91. In FIG. 9C, reservoir cell 99 contains a sample preparation chamber 100 which is separated from the sensing solution 91 by a porous plate or membrane 101. The sample is placed into sample preparation chamber 100 which is surrounded by heating coil 102 for heating the sample to produce a sample product (e.g. vaporizing, melting or reacting the sample) which permeates through plate or membrane 101 into the sample solution 91. Reservoir cell 103 of FIG. 9D combines the features of FIGS. 9B, C Cell 103 has a sample chamber 104 separated from sensing solution 91 by porous plate or membrane 105 and a solvent chamber 106 separated from sample chamber 104 by porous plate or membrane 107. A sample in solid form is placed in sample chamber 104 and a leaching solution is introduced into chamber 106 through port 108 which is controlled by valve 109. The solution passes through plate or membrane 107 into sample chamber 104 which is also heated by surrounding heating coil 110. The pre-treated sample passes through plate or membrane 105 emptying into sensing solution 91. Other sample pretreatment may be performed in a sample preparation chamber (e.g., creating excited states, photolysis, radiation, oxidation, reduction or chemical reactions).

Figure 10:
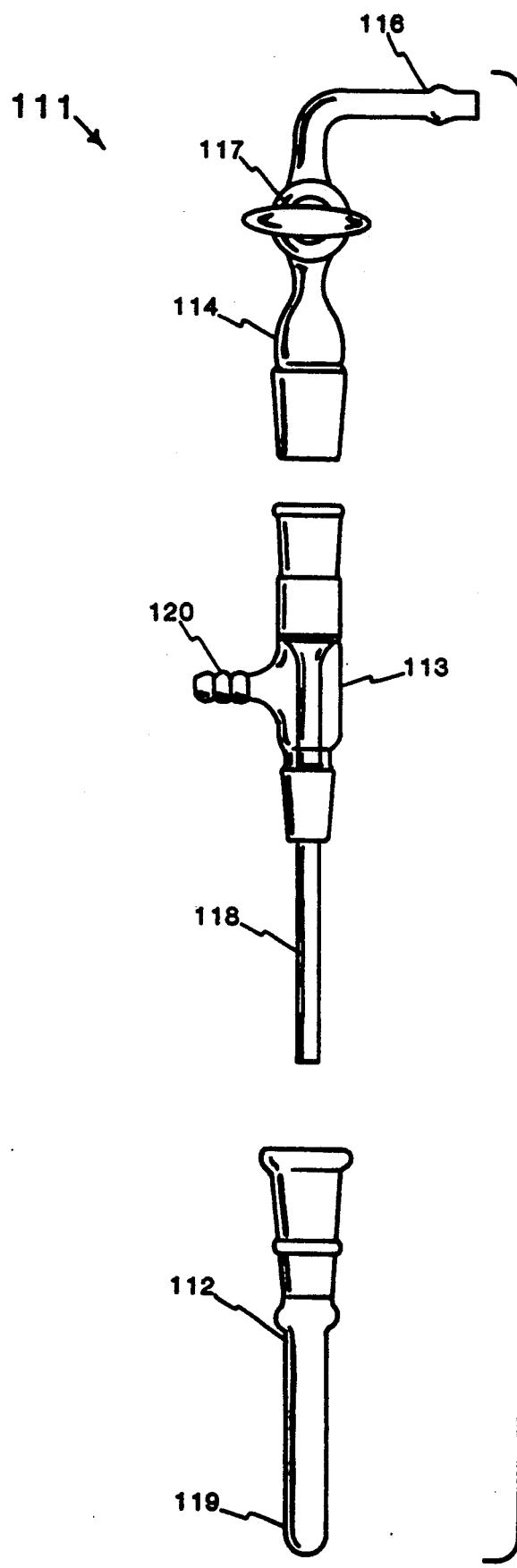
FIG. 10 is an assembly drawing of a reservoir cell made of standard laboratory glassware.

An illustrative example of a removable reservoir cell made from standard laboratory glassware is shown in FIG. 10. Cell 111 is formed by connecting test tube (with ground glass joint) 112, vacuum adaptor 113 and adaptor (with valve) 114. A gaseous sample is inlet through inlet 116 and its flow is controlled by valve 117. The sample flows down through tube 118 which extends into test tube 112 which contains the sensing reagent solution. Tube 118 extends down into test tube 112 below the level of the sensing solution so that the gaseous sample is bubbled through the solution. The sample then passes up through test tube 112 in the annular region outside tube 118 and is drawn from the cell through outlet 120 which is attached to a vacuum or suction source. Test tube 112 is placed in the sensor body or holder as previously described. The lower portion 119 of test tube 112 below tube 118 is the portion of cell 111 around which the source and detector are positioned.

In accordance with the invention, a reservoir chemical sensor with a removable cell is provided which allows great ease in using the sensor for different chemistries. The cell can be of good optical quality with optically flat surfaces for the most precise measurements. For less precise measurements, cheaper plastic cells are available. Standard laboratory "cuvettes" can be utilized. Typical internal dimensions of a cell are 1 cm×1 cm×3 cm with a wall thickness of 1 mm. The cell fits into a holder which is 2.5 cm×2.5 cm×3 cm. The cells can be made of plastic, glass or quartz or any other optically transparent material at the wavelength of the sensing reaction. Suitable light sources include diodes, lasers and lamps and a suitable detector is a photodiode. Virtually any chemistry can be used in the invention, and any measurement technique, including luminescence, absorption, reflection, refraction, Raman and scattering. Particular details which relate to the invention, particularly regarding specific chemistries; measurement techniques; sources, detectors, and their operation; membranes; and sample pretreatment, are found in U.S. patent application Ser. No. 544,681 filed June 27, 1990, which is herein incorporated by reference.

Changes and modifications, in the specifically described embodiments can be carried out without departing from the scope of the invention which is intended to be limited only by the scope of the appended claims.

I claim:

1. A reservoir chemical sensor, comprising:
   a miniaturized sensor body;
   a reservoir cell channel formed in the sensor body;
   a removable reservoir cell which removably fits snugly in the reservoir cell channel in the sensor body;
   at least one illumination source channel formed in the sensor body and communication with the reservoir cell channel;
   at least one diode illumination source mounted in an illumination source channel in the sensor body around the reservoir cell channel for inputting optical signals into the reservoir cell;
   at least one detector channel formed in the sensor body and communicating with the reservoir cell channel;
   at least one photodiode detector mounted in a detector channel in the sensor body around the reservoir cell channel for detecting optical signals from the reservoir cell.

2. The reservoir chemical sensor of claim 1 further comprising a sensing solution in the reservoir cell.

3. The reservoir chemical sensor of claim 1 wherein at least one source and at least one detector are oriented in a substantially linear face-to-face arrangement.

4. The reservoir chemical sensor of claim 1 wherein at least one source and at least one detector are oriented in a substantially orthogonal orientation.

5. The reservoir chemical sensor of claim 1 wherein at lease one detector is oriented in a substantially linear face to-face arrangement with at least one source, and at least one detector is oriented substantially orthogonally to the at least one source.

6. The reservoir chemical sensor of claim 5 further comprising a dichroic mirror positioned in the reservoir cell to pass one optical signal to the at least one substantially linear detector and to pass another optical signal to the at least one substantially orthogonal detector.

7. The reservoir chemical sensor of claim 5 further comprising a beam splitter positioned in the reservoir cell to pass one optical signal to the at least one substantially linear detector and to pass another optical signal to the at least one substantially orthogonal detector.

8. The reservoir chemical sensor of claim 1 further comprising a converging lens mounted in the sensor body between the reservoir cell and at least one of the at least one source and the at least one detector.

9. The reservoir chemical sensor of claim 1 further comprising a diverging lens mounted in the sensor body between the reservoir cell and at least one of the at least one source and the at least one detector.

10. The reservoir chemical sensor of claim 1 further comprising a color filter mounted in the sensor body between the reservoir cell and at least one of the at least one source and the at least one detector.

11. The reservoir chemical sensor of claim 1 wherein the reservoir cell has a cross-sectional shape selected from square, rectangular, circular or triangular.

12. The reservoir chemical sensor of claim 1 wherein the reservoir cell further comprises a semi-permeable membrane on a surface thereof for passing a species of interest into the cell while containing a sensing solution therein, and the sensor body further comprises a sample flow channel formed therein and communicating with the membrane so that a sample fluid can contact the membrane.

13. The reservoir chemical sensor of claim 12 further comprising a second semi-permeable membrane on an opposed surface of the reservoir cell and a second sample flow channel formed in the sensor body and communicating with the second membrane to provide a pass through cell.

14. The reservoir chemical sensor of claim 1 further comprising an inlet pipe extending into the reservoir cell for bubbling a gaseous sample through a sensing solution in the cell and an outlet pipe extending from the cell for removing the sample.

15. The reservoir chemical sensor of claim 1 further comprising a sample pretreatment chamber at the top of the reservoir cell.

16. The reservoir chemical sensor of claim 15 wherein the sample pretreatment chamber is separated from a sensing solution in the reservoir cell by a porous plate or membrane.

17. The reservoir chemical sensor of claim 16 further comprising an electrical heating coil around the sample pretreatment chamber.

18. The reservoir chemical sensor of claim 16 wherein the sample preparation chamber comprises a sample holding chamber, a solvent holding chamber above the sample holding chamber, a porous plate or membrane separating the sample holding chamber from the solvent holding chamber, and solvent inlet means in the solvent holding chamber.

19. The reservoir chemical sensor of claim 18 further comprising an electrical heating coil around the sample holding chamber.

20. The reservoir chemical sensor of claim 1 wherein the reservoir cell is made of glass, quartz, plastic or any other optically transparent material at the light wavelength of the optical signals detected.

* * * * *